United States Patent [19]

Sapko et al.

[11] Patent Number: 4,799,799
[45] Date of Patent: Jan. 24, 1989

[54] DETERMINING INERT CONTENT IN COAL DUST/ROCK DUST MIXTURE

[75] Inventors: Michael J. Sapko, Finleyville; Jack A. Ward, Jr., Oakmont, both of Pa.

[73] Assignee: The United States of America as represented by the Secretary of the Interior, Washington, D.C.

[21] Appl. No.: 943,347

[22] Filed: Dec. 19, 1986

Related U.S. Application Data

[63] Continuation-in-part of Ser. No. 699,514, Feb. 6, 1985.

[51] Int. Cl.[4] .............................................. G01N 21/55
[52] U.S. Cl. .................................... 356/446; 356/448
[58] Field of Search ................. 356/448, 445, 446, 447

[56] References Cited

U.S. PATENT DOCUMENTS

| | | | |
|---|---|---|---|
| 1,894,808 | 1/1933 | Witte | 356/448 |
| 1,894,809 | 1/1933 | Witte | 356/448 |
| 3,610,205 | 10/1971 | Rarey | 356/445 |
| 4,566,798 | 1/1986 | Haas | 356/448 |

OTHER PUBLICATIONS

Arkin et al *Statistical Methods* Fifth Edition (1970) College Outline Series, Barnes & Noble, Inc. New York pp. 100-101.

*Primary Examiner*—Richard A. Rosenberger
*Attorney, Agent, or Firm*—E. Philip Koltos

[57] ABSTRACT

A method and apparatus for determining the inert content of a coal dust and rock dust mixture uses a transparent window pressed against the mixture. An infrared light beam is directed through the window such that a portion of the infrared light beam is reflected from the mixture. The concentration of the reflected light is detected and a signal indicative of the reflected light is generated. A normalized value for the generated signal is determined according to the relationship $$\phi = (\log i_c - \log i_{co}) / (\log i_{c100} - \log i_{co})$$

where
$i_{co}$ = measured signal at 0% rock dust
$i_{c100}$ = measured signal at 100% rock dust
$i_c$ = measured signal of the mixture.

This normalized value is then correlated to a predetermined relationship of $\phi$ to rock dust percentage to determine the rock dust content of the mixture. The rock dust content is displayed where the percentage is between 30 and 100%, and an indication of out-of-range is displayed where the rock dust percent is less than 30%. Preferably, the rock dust percentage (RD%) is calculated from the predetermined relationship $$RD\% = 100 + 30 \log \phi.$$

where the dust mixture initially includes moisture, the dust mixture is dried before measuring by use of 8 to 12 mesh molecular-sieves which are shaken with the dust mixture and subsequently screened from the dust mixture.

7 Claims, 3 Drawing Sheets

DETERMINING INERT CONTENT IN COAL DUST/ROCK DUST MIXTURE

RELATED APPLICATION

This application is a continuation-in-part of application Ser. No. 699,514 filed Feb. 6, 1985.

FIELD OF THE INVENTION

The present invention relates generally to the determining of the inert content in coal dust, and more particularly to an electro-optical method for determining the concentration of rock dust in a coal dust and rock dust mixture.

BACKGROUND OF THE INVENTION

Many years of research by the Bureau of Mines and others have shown that the mixing of a sufficient quantity of inert dust with coal dust will prevent coal dust explosions. Rock dust or limestone dust is the most common inert dust used. This inerting technique, referred to as rock dusting, is required by law in U.S. underground coal mines. At the present time, the coal dust-rock dust mixture is required by law to be at least 65% in all working areas (except the first 40 ft. from the face) and 80% in returns. In the presence of methane, the incombustible content of the dust must be increased by 0.4 and 1 pct., respectively, for each 0.1 pct. methane in the ventilating air.

In assuring compliance with the law, inspectors currently collect samples of deposited dust, in any given mine, every 200 ft. of entry once every 2 months. The conventional sample is a 6 inch wide band across the floor, ribs and roof to a depth of 2 inches, where possible. If the floor is well rock dusted but the roof and ribs are determined visually to be deficient in rock dust content, then it is recommended that the combined rib and roof portion of the band sample be kept separate from the floor portion so that a separate analysis can be run on each. The inspector screens the sample through a sieve and sends about 200 g of the sieved samples to Mt. Hope, WV for chemical analysis. The inspector also screens the sample through a No. 10 sieve, if possible, and also sends about 200 g of this sieved sample to Mt. Hope WV for analysis. The concentration of rock dust in the sample is obtained with volumetric methods by measuring the inverse in the volume of alcohol used in a volumeter. From this rock dust measurement, the incombustible content is computed. All borderline samples then undergo a more accurate low temperature ashing procedure.

Typically, the results of the analysis are received about 2 weeks after the sample is taken. In the meantime, the mine operators must rely on visual inspection (dark or light) of rock dusted areas to estimate the quality of the rock dusting practice on a day-to-day basis.

In the prior art, there have been various devices disclosed for detecting particle concentrations. For example, in U.S. Pat. No. 3,610,205 (Rarey), an apparatus for measuring and controlling the mixture content in an electrostatic printer is disclosed. This apparatus includes a window adjacent the path of movement of the mix of component particles which contacts the particles in transent therepast. The degree of reflected light depends upon the ratio of the component particles which differ in optical qualities.

In U.S. Pat. No. 3,872,825 (Davidson), an apparatus for detecting particle concentration in a mix of carrier granules and toner particles in a copying machine is disclosed. This apparatus includes a reflecting means which attracts toner particles thereto electrostatically. A beam of light rays is directed to the reflecting means and the concentration of the reflected beam indicates the concentration of toner particles 0 on the reflector surface which is a function of the toner particles in the mixture.

In U.S. Pat. Nos. 3,564,263 (Shaw) and 3,810,617 (Steinberg), apparatuses for determining the concentration of particles in a fluid stream are disclosed. The apparatuses use light rays which are directed through the stream.

SUMMARY OF THE INVENTION

In accordance with the present invention, a method and apparatus for determining the inert content in a coal dust and rock dust mixture is provided. Ths determination is made by pressing a transparent window against the mixture and directing an infrared light beam through the transparent window onto the mixture. The infrared light which is reflected back through the transparent window is detected and a signal indicative thereof is generated. The signal is then normalized with normalized value $\phi$ determined according to the relationship $$\phi = (\log i_c - \log i_{co})/(\log i_{c100} - \log i_{co})$$

where
 $i_{co}$ = measured signal at 0% rock dust
 $i_{c100}$ = measured signal at 100% rock dust
 $i_c$ = measured signal of the mixture This normalized value is then correlated with a predetermined relationship of $\phi$ to rock dust percentage to determine the rock dust content of the dust mixture.

According to the preferred embodiment of the present invention, the calculating of rock dust percentage (RD%) is according to the predetermined relationship $$RD\% = 100 + 30 \log_e \phi.$$

In addition, a display is provided for displaying the rock dust percentage where the percentage is between 30 and 100%, and for displaying an indication of an out of range condition where the rock dust percentage is less than 30%.

In use, the apparatus must be initially calibrated for the particular rock dust and coal dust found in the sample. This is done by measuring pure samples of the rock dust and coal dust. Where the rock dust and coal dust mixture includes moisture, the dust mixture is dried. This is accomplished by shaking the dust mixture with 8 to 12 mesh molecular-sieves and subsequently passing the sieve and dust mixture through a 60-mesh sieve to separate the molecular-sieves and large dust particles from the remainder of the dust mixture.

It is an advantage of the present invention that a quick and reliable method for determining the rock dust content in a coal dust-rock dust mixture is provided which can be used in an underground mine or roadway or in an area immediately adjacent to the mine such as a mine office.

It is also an advantage of the present invention that a completely safe method of determining inert content of a dust mixture is provided, and that this determination can be made with very small sample sizes.

It is a further advantage of the present invention that the apparatus used makes use of standard off-the-shelf electronic components and that the apparatus can be manufactured at low cost.

Other features and advantages of the present invention are stated in or apparent from a detailed description of presently preferred embodiments of the invention found hereinbelow.

DETAILED DESCRIPTION OF THE PREFERRED EMBODIMENTS

The method of the present invention is based upon the measurement of light reflected from a surface made up of a mixture of dark coal dust and light rock dust particles. The amount of light reflected from the surface of the sample increases with an increase in the number of rock dust particles in the sample in a way that can be related to the percentage of rock dust in the sample.

Figure 1:
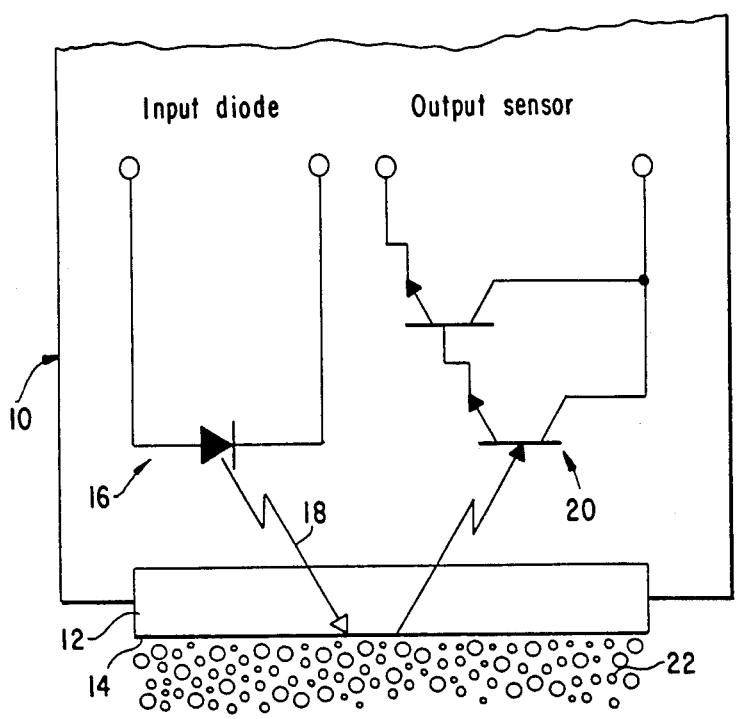
FIG. 1 is a schematic elevation view of he end of the held-held probe used with the present invention.

With reference now to the drawings in which like numerals represent like elements , the end of a hand-held probe 10 is depicted schematically in FIG. 1. As shown, the end of hand-held probe 10 includes a transparent window 12 including a flat outer surface 14. Located adjacent and on one side of transparent window 12 is a light emitting diode 16. Preferably, light emitting diode 16 is a gallium arsenide LED which radiates infrared light upon activation. As shown, light emitting diode 16 emits a light beam 18 toward transparent window 12. Located on the other side of hand-held probe 10 from light emitting diode 16 is a photodetector (Darlington) 20. A suitable reflective object sensor of this type is OPB 730 manufactured by Optron, Inc.

It is envisioned that hand-held probe 10 will be relatively small in nature, for example, having a cross section of approximately ½". In addition, transparent window 12 is preferably a 0.13 inch thick by 0.39 inch diameter quartz window. In FIG. 1, transparent window 12 is shown pressed up against a dust mixture 22 containing rock dust and coal dust.

In operation, hand-held probe 10 functions in the following manner. Initially, a sample of dust mixture 22 is gathered in a location where it is possible to press transparent window 12 of hand-held probe 10 against dust mixture 22. With a slight pressure applied to hand-held probe 10, the particles of dust mixture 22 align and thus establish a uniform reflecting surface adjacent flat outer surface 14 of transparent window 12. Light emitting diode 16 is then activated to direct an infrared light beam 18 toward transparent window 12. When light beam 18 reaches flat outer surface 14, a portion of light beam 18 is reflected by dust mixture 22 back through transparent window 12 to photodetector 20. This reflected light causes photodetector 20 to produce a current flow which is proportional to the amount of reflected radiation. The amount of reflected radiation is also proportional to the percentage of rock dust in dust mixture 22.

Figure 3:
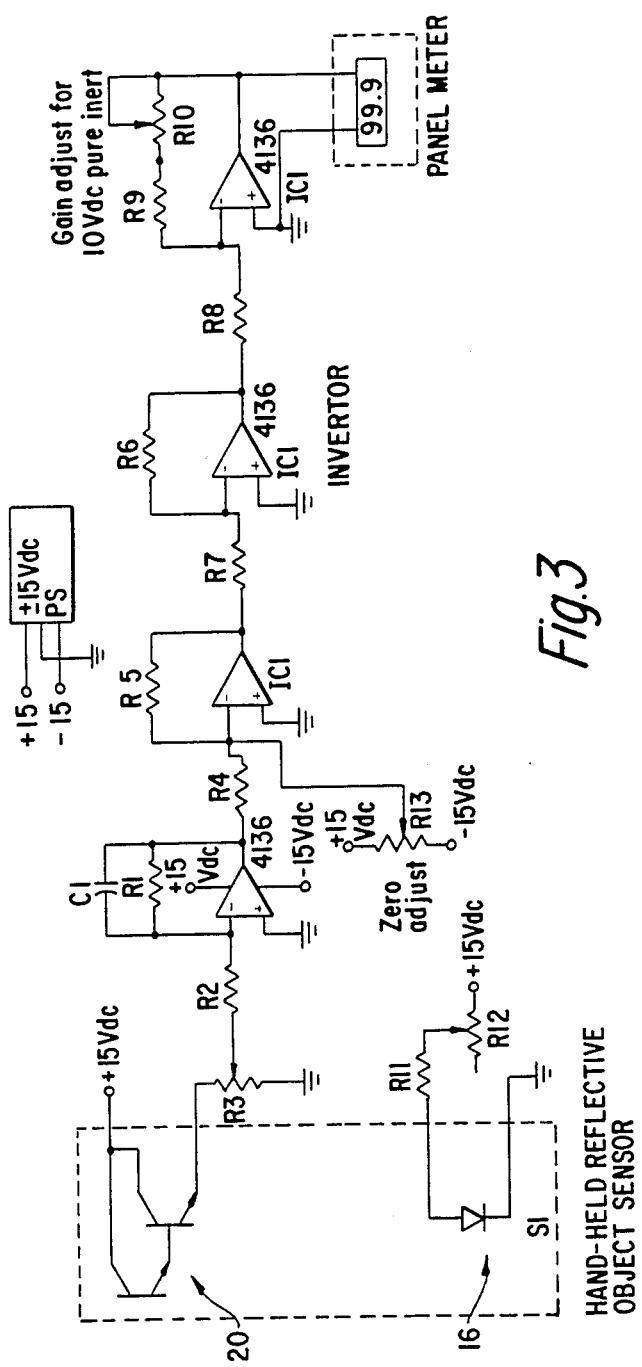
FIG. 3 is a schematic wiring diagram of the concentration detector of the present invention.

The signal from photodetector 22 is fed into a simple operational amplifier circuit as depicted in FIG. 3 where the output is adjusted to read 0 for pure coal dust and 100% for pure rock dust. The circuit parameters shown in FIG. 3 produce a 10 volt DC output for pure rock dust and 0.0 volts DC output for pure coal dust.

Figure 2:
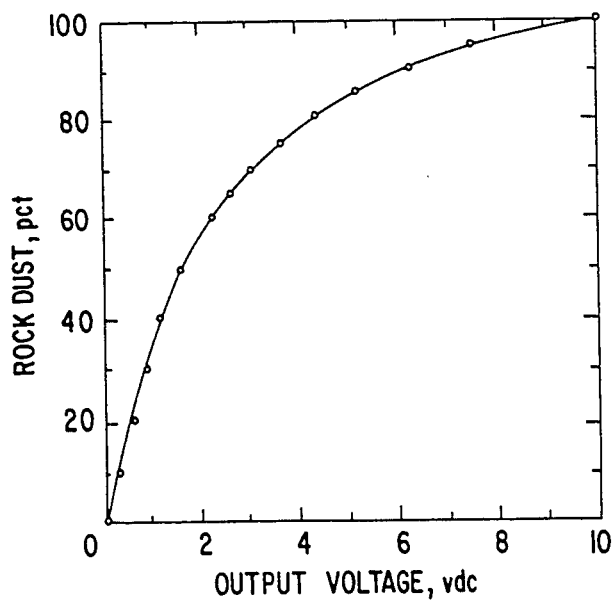
FIG. 2 is a graphical representation of the correlation between the percentage of rock dust in a dust mixture and an output voltage produced by reflected light concentrations.

A typical calibration curve of voltage output versus rock dust content is depicted in FIG. 2. The curve depicted in FIG. 2 is typical of the calibration curves for various mines and it has been found that this curve does not vary much from mine to mine. Thus, in operation, a calibration curve similar to that in FIG. 2 is first established using dust mixtures from a particular mine of pure coal dust and pure rock dust. Thereafter, when the probe is inserted into a small quantity of dust mixture 22, the output voltage of the operational amplifier is determined. This reading is then converted to percentage rock dust easily by means of the calibration curve.

Where dust mixture 22 also contains significant quantities of moisture, it is necessary to dry dust mixture 22 before the percentage of rock dust can be determined. In order to accomplish this, a quantity f dust mixture 22 is simply shaken with an equal quantity of molecular seives (4 angstrom, 8-12 mesh beads). Thereafter, the determination is easily made.

It should also be appreciated that it would be possible to use miniaturized electronics to include light emitting diode 16, photodetector 20, the operational amplifier and the readout meter into a single self-contained unit, perhaps the size of an ordinary fountain pen. In addition, it would also be possible through the use of additional electronic circuitry to provide for a direct readout in terms of rock dust content, thus eliminating the need for referring to a calibration curve. Experience has also shown that only two data points are required to produce a calibration of the instrument which would have sufficient accuracy for immediate coal dust-rock dust concentration measurement for safety checks.

Although providing a restricted range, the following embodiment of the present invention is particularly advantageous. This embodiment is based on the fast discussed above that coal dust has a low infrared reflectivity, whereas rock dust has a high reflectivity. Therefore, the surface reflectivity of a mixture of these two materials is to first order, proportional to their volumetric ratios. Thus, the intensity of the reflected radiation ($I_\omega$) is proportional to the radiation reflected by the rock dust plus that reflected by the coal dust. Each of these terms is the product of the incident radiation intensity at the dust surface ($I_o$), the fraction of the irradiated surface area that is rock dust ($f_r$) or coal dust ($f_c$) and the emissivity ($\epsilon$) of the respective material, i.e., $I_\omega 32\ I_o(f_r\epsilon_r+f_c\epsilon_c)$, or since $f_r+f_c=1$ then $I_\omega/I_o=\epsilon_c+f_r(\epsilon_r-\epsilon_c)$. This assumes that the dust is made up of hard non-compactible monosized spheres and that no light is lost between the packed spheres. If $f_r=1$, i.e., 100 pct rock dust, then $I_\omega=I_{100}=I_o\epsilon_r$, and the equation is rewritten in a slightly different form to expedite future calculations:

$$I_\omega/I_{100}=\epsilon_c/\epsilon_r+f_r(1-\epsilon_c/\epsilon_r) \qquad (1).$$

If the fraction of surface is proportional to the effective cross-sectional area of spherical particles, equation (1) is written as $$I_\omega = N_r \pi R_r^2 (1-\epsilon_c/\epsilon_r)/(N_r \pi R_r^2 + N_c \pi R_c^2) + \epsilon_c/\epsilon_r \quad (2)$$

where N, $\epsilon$, and R are the particle number density, particle reflectivity, and effective particle radius, respectively, and the subscripts r and c stand for rock dust and coal dust, respectively. If x is the mass fraction of rock dust, and $\rho_r$ and $\rho_c$ are the particle densities of rock dust and coal dust, then $$x = N_r \rho_r R_r^3/(N_r R_r^3 \rho_r + N_c \rho_c R_c^3) \quad (3).$$

Equation (3) for the intensity ratio is rewritten $$I_\omega = R_c \rho_c x (1-\epsilon_c/\epsilon_r)/(R_c \rho_c x + R_r \rho_r (1-x)) + \epsilon_c/E_r \quad (4) \text{ or}$$

$$I_\omega = x(1-\epsilon_c/\epsilon_r)/(x+k(1-x)) + \epsilon_c/\epsilon_r \quad (5)$$

where $$K = R_r \rho_r/(R_c \rho_c) \quad (6).$$

This simple theory fits the experimental measurement discussed subsequently rather well.

The actual radiation incident on the optical detector is the fraction of the radiation reflected from the dust layer, namely that portion collected and focused on the the detector by the optics plus a portion due to background radiation ($I_b$) not related to the LED radiation plus a portion due to scatter of the LED radiation within the system optics ($I_s$), e.g., off the probe window. Therefore $$I_c = I_b + I_\omega + I_s \quad (7)$$

Two types of coal dust-rock dust (CD-RD) mixtures were studied in experiments: (1) those carefully prepared from bulk coal that was ground, dried, and sieved under controlled laboratory conditions, which are referred to as prepared samples, and (2) samples taken by mine inspectors from different mines and shipped to the Bureau of Mines laboratories in plastic bags, which are referred to as mine samples. The prepared samples were accurate to ±0.1 pct rock dust (RD). Considerable care was exercised to ensure that the mixture was homogeneous. The coal used in the preparation of prepared samples came from the Bruceton Experimental Mine. This coal was pulverized so as to contain 80 wt pct of particles less than 75 μm (200 mesh). The particle surface weighted mean diameters ranged from 25 to 30 μm. The RD came from a local distributor and contained particles about 74 wt pct less than 74 μm and had a surface weighted mean diameter range from 15 to 20 μm.

The bulk of the experiments used to measure the surface reflectivity of CD-RD mixtures as a function of RD concentration made use of a TRW Corp. OPB707A optical sensor, which consisted of an infrared (950±20 nm) LED (GaAlAs) transmitter and a photo Darlington (Silicon) infrared (950±30 nm) receiver housed in a single cubical unit measuring approximately 3 mm on edge. Optical cross talk between the LED and photo Darlington within the sensor housing was minimized through the use of an optically opaque partition separating the transmitter from the receiver.

Using optical neutral density filters to attenuate the radiation for the LED, it was found that the photo Darlington collector current ($i_c$), is proportional to the infrared intensity at the LED wavelength (although the constant of proportionality varies considerably, by as much as a factor 20, between sensors). Therefore, $i_c = i_d + i_\omega + i_b + i_s$, where $i_d$ is the photo Darlington dark current, $i_\omega$ the current associated with the radiation reflected by the dust surface, and $i_s$ and $i_b$ are the collector currents associated with scattered and background radiation respectively. On the average $i_s = 5$ μa, $i_d = 200$ μa and $i_b << i_d$. Since $i_c \, 100 \leq$ μa, $i_d$, $i_b$ and $i_s$ can be neglected in comparison and $i_c/i_{c100} = I_\omega/I_{\omega100}$ or $i_c = I_\omega$ 8)

where $i_{c100}$ is the collector current for 100 pct RD.

To expedite conducting the reflectivity measurement of dusts using this sensor, it was incorporated in a Teflon holder, or probe. With this arrangement, the sensor had a surface viewing area (i.e., the overlap of the area irradiated by the LED and seen by the photo Darlington) of 49 mm². To conduct a measurement using this probe, about 1 inch of the CD-RD mixture was placed in a 1 inch diameter plastic vial and the quartz window end of the probe was pressed into the dust, and the $i_c$ recorded. Following each test, the probe was carefully wiped clean of any dust with a soft dry cloth to prevent contaminating the other mixtures. It was observed that the quartz-dust interface reflected a significant portion of radiation back to the photo Darlington, resulting in an additional photo Darlington bias current, $i_s$. However, this additional bias current did not contribute any measurable error to the results.

The first study in this series of experiments concerned mesurement of the sensor's photoelectrical characteristics as a function of collector to emitter voltage. The $i_c$ and $V_{ce}$ were measured for various RD mixtures using a fixed value of the probe LED current, 2 ma. A typical set of characteristic traces were obtained using Pittsburgh pulverized coal dust (PPCD)-RD prepared mixtures. These curves closely resembled those characteristic traces for photo transistors, with the obvious exception that the traces were shown as a function of pct rock dust rather than base irradiance. To compare these results with the above theory (assuming $\epsilon_c << \epsilon_r$), a load line was constructed (although a 500 Ω load was used, the exact value of the resistive load is independent of the results), and determined the $i_c$ values at the intersection of the load line and the characteristic traces. A comparison of the measured and theoretical $i_c/i_{c100}$ values as a function of percent RD was made. It was shown that the theoretical curve corresponds to a least square value for k (equation (6)) that the theory is in satisfactory agreement with experiment, i.e. with ±4 pct RD.

Since the intent was to construct an analog rock dust mater, it is most desirable to obtain a linear relationship between percent RD and a measureable function $i_c$. Thus, by experimenting with various functional relationships involving $i_c$, one was found which was suited for this purpose, namely, $$\phi = (\log i_c - \log i_{co})/(\log i_{c100} - \log i_{co}) \quad (9)$$

where $i_{co}$ and $i_{c100}$ are the measured collector currents for 0 and 100 pct RD respectively, and $i_c$ is the current at any other percent RD.

A plot of percent RD vs log ($\phi$) respectively for a prepared sample of Arkwright Mine CD-RD mixtures is obtaining a linear relation between percent RD and a measurable function of $i_c$, viz., log ($\phi$) between 30 and 100 pct RD. Furthermore, the $\phi$ normalization also minimizes the error due to the photo Darlington's gain change with temperature, and as evidenced by the discussion below of the results of the mine samples' reflectivity measurements, the log ($\phi$) function also has an improved linearity in the vicinity of 100 pct RD.

This renormalization technique makes the method a viable technique for determining the rock dust content of coal dust-rock dust mixtures. Without this normalization, use in the mining industry would not be possible because of variations in coal and particularly rock dust reflectivity. Based on this definition of $\phi$, a circuit is used to take advantage of the well known exponential relation between the current ($i_d$) through and voltage drop ($V_d$) across a diode, to obtain a direct measurement of log ($i_c$). Since $i_d = i_{do} \exp(kV_d)$, where $i_{do}$ and k are constants for a given diode at a fixed temperature, $\ln(i_d) = \ln(i_{do}) + kV_d$. Substituting this expresion in the definition of $\phi$ above, $$\phi = (V_d - V_{do})/(V_{d100} - V_{do}), \qquad (10)$$

where $V_{do}$ and $V_{d100}$ refer to diode voltages corresponding to 0 to 100 pct RD respectively.

For the 1N914 diodes used, the relation $i_d = i_{do} \exp(kV_d)$ was found to be accurate within 7 pct at 95 pct confidence over the range $0.4v < V_d < 0.7v$ or equivalently $20 \mu a \leq i_d \leq 6$ ma. A comparison of percent RD as a function of the diode voltage for prepared Arkwright CD-Rd mixtures was made using four different sensors. It was evident from this comparison that, as discussed above, different sensors have a pronounced effect on the relationship between pecent RD and $V_d$. However, renormalization to log ($\phi$) causes this disparity to be eliminated (at least in the 30 to 100 pct RD range).

The moisture content of the dust mixtures was also found to influence the reflectivity mesurements as was also discussed above. The effect of added moisture on reflectivity measurements is to increse the measured percentage of RD. As in the case of the particle size factor, the renormalization does not correct for moisture. Therefore, the test samples must be dried prior to making a reflectivity measurement. In current rock dust surveillance practices, wet samples are seldom taken and when they are, chemical analysis is much longer and more involved than if the samples were dry. According to the present invention, a technique has been developed for making on-the-spot rock dust measurements with samples containing significant amounts of excess water. The techniques used inexpensive reusable pea size molecular sieves to dry the sample. A unique feature of the sieve is the ability to separate the adsorbate (H$_2$O) on the basis of molecular size and configuration. Thus, 4 Angstrom sieves will selectively take up water which has a critical molecular diameter of 3.2 angstroms without disturbing the dust particles. Depending on mixing times, the molecular-sieves extract both surface and bound moisture.

In practice, the dust sample is placed in a vial along with 8 to 12 mesh molecular-sieves and shaken for 2 to 3 minutes. When the sample is dry, as evidenced by its free flow, it is passed through a 60-mesh sieve which removes the molecular-sieves and any large dust particles. By making reflectance measurements of both the wet and dried samples, one can, in parinciple, determine both the rock dust content and the excess water.

Experiments were conducted using the mine dust samples. The samples were received in plastic bags, each containing about 200 g of dust along with a sample of pure CD and pure RD taken at each mine. Portions of these samples were analyzed for moisture and incombustibles. Given the coal's percent incombustible and moisture associated with each mine, the percent RD in each sample is calculated from the following relation:

$$\%RD = (A + M - TIC)/(A + M)/100) - 1) \qquad (11)$$

where A is the percent ash in the coal, M is the percent bound moisture, and TIC is the percent total incombustible as determined by chemical analysis. Prior to measuring the sample's reflectivity, each pre-dried sample was passed through a minus 20 mesh sieve as required by law for the chemical analysis. Plots of percent RD against log ($\phi$) for all four mines were made. The regression lines for the individual mine were statistically indistinguishable at a 0.95 pct confidence level. In addition, unlike the prepared samples, the mine samples exhibited considerable scatter in the measurement. The reasons for this are believed to be due to uncertainties in the chemical analysis, the presence of foreign reflecting material, (e.g., dirt), and differences in particle size distribution. The least squares best fit line, (i.e., pecent RD = 100 + 30 log$_e$ ($\phi$) forced through the (100,0) point), showed a standard error of regression of 7 pct RD at a 95 pct confidence level. This is considered adequate for the sample screening purposes for the present invention is intended.

Figure 4:
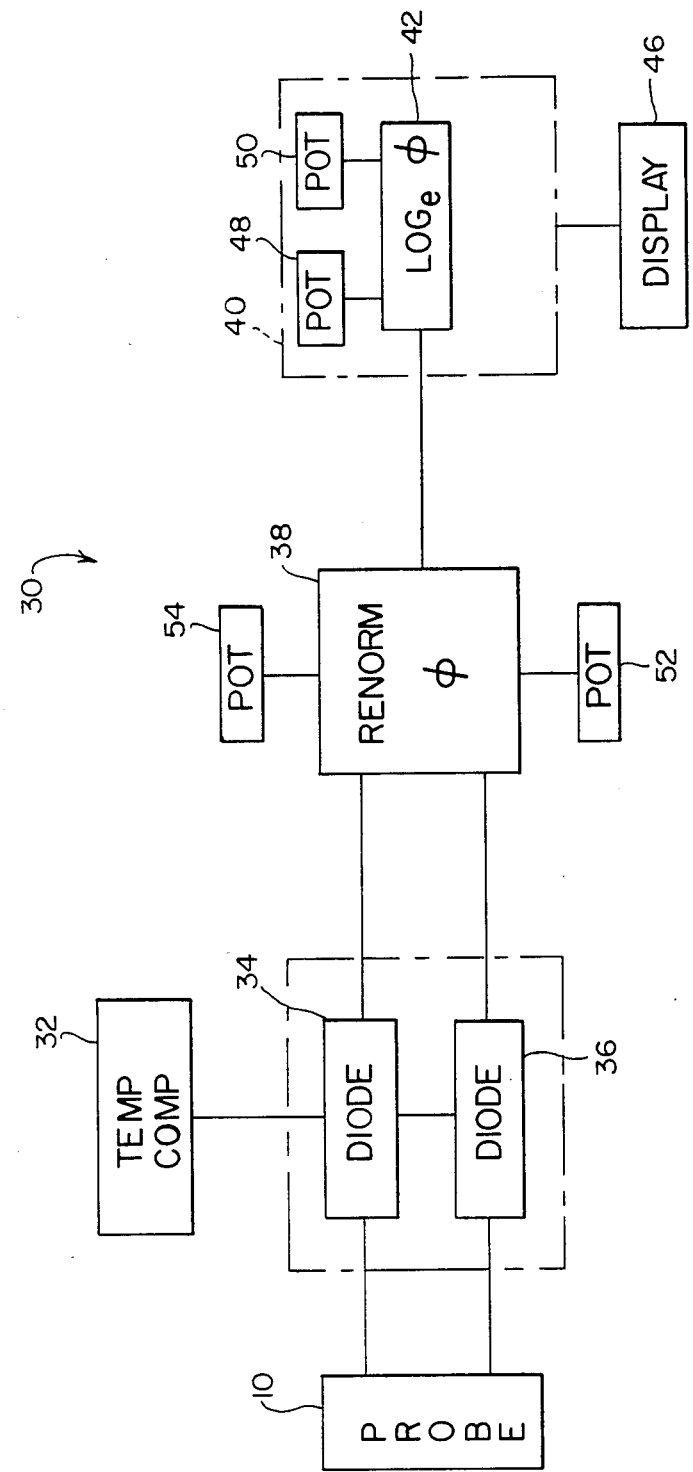
FIG. 4 is a schematic circuit black diagram of an analog rock dust meter according to the present invention.

FIG. 4 shows a circuit 30 for an analog rock dust meter according to the present invention discussed above. A first stage 32 provides temperature compensation for emitter diode 34. Circuit 30 is essentially the same as that used in the reflectivity test configuration discussed above except for the addition of a second diode 36. Both diodes 34 and 36 are physically located in the same transistor array IC package. A second stage 38 calculates the renormalization function $\phi$, and a third stage 40 consists of a log$_e$ IC chip 42 to generate log ($\phi$). Circuit 30 draws about 15 ma and with a suitable power pack shown, and provides about 4 hours of continuous service. Since the actual time required to conduct a test using the rock dust meter is on the order of 1 minute, under mine conditions the unit should be good for about 250 tests before requiring a recharge. This should be adequate for a typical mine inspector's day's work.

Circuit 30 shown in FIG. 4 is designed to provide accurate values of pct RD over the linear portion of the pct RD vs log$_e$ ($\Omega$) relationship, viz., 30 to 100 pct RD. When the probe is placed in mixtures having rock dust percentages less than 30 pct, LCD 46 displays a minus 1, indicating an out-of-range value.

Before the meter can be used, log chip 42 must first be adjusted, using potentiometers 48 and 50 to reproduce the pct RD vs loge ($\phi$) linear relationship, viz., pct RD = 100 + 30 log ($\phi$). The procedure for performing this adjustment is contained in the manufacturers' data sheets. This adjustment is done only once and need not be repeated unless the log chip has to be replaced.

There is another calibration step, however, that must be repeated at each mine site. This requires inserting the probe successively samples of pure rock dust and pure coal dust and adjusting potentiometers 52 and 54 so that LCD display 46 displays 100 and minus 80 respectively (minus 80 corresponds to the pure coal dust).

After calibration, the rock dust meter was tested by measuring the percent RD in prepared PPCD-RD samples. The results showed the desired ideal rock dust meter response, and it was apparent that the rock dust meter provides pct RD values accurate to within ±2 pct in the range 30 to 100 pct RD for prepared samples. Similar measurements conducted using the mine samples also showed that the ideal rock dust meter performance line falls squarely through the center of the cluster of points corresponding to each mine, i.e., the ideal rock dust meter line is statistically indistinguishable (for an $\alpha = 0.95$) from the data's best linear regression.

Experiments were conducted with rock dust meters of the present invention to demonstrate the interchangeability of probes. Again, with the normalization procedure, the data clustered around the ideal rock dust meter line, and statistically there was no indication that any probe was any better or worse than any other.

Although the present invention has been described with respect to an exemplary embodiment thereof, it will be understood by those of ordinary skill in the art that variations and modifications can be effected within the scope and spirit of the invention.

I claim:

1. A method of determining the inert content in a coal dust and rock dust mixture comprising the steps of: providing a transparent window at an end of a probe; pressing the transparent window of the probe against the mixture;
   directing an infrared light beam from inside of the probe onto the mixture through the transparent window such that a portion of the infrared light beam is reflected from the mixture;
   detecting the concentration of the reflected light;
   generating a signal indicative of the reflected light;
   determining a normalized value ($\phi$) for the signal generated according to the relationship $$\phi = (\log i_c - \log i_{c0})/(\log i_{c100} - \log i_{c0})$$

where
   $i_{c0}$ = measured signal at 0% rock dust
   $i_{c100}$ = measured signal at 100% rock dust
   $i_c$ = measured signal of the mixture; and
   correlating the normalized value to a predetermined relationship of $\phi$ to rock dust percentage to determine the rock dust content of the mixture wherein the correlating step includes the calculating of rock dust percentage (RD%) from the predetermined relationship.

$$RD\% = 100 + 30 \log_e \phi.$$

2. A method for determining inert content in a mixture as claimed in claim 1 wherein the dust mixture also includes moisture, and further including the step of drying the dust mixture before the pressing step.

3. A method for determining inert content in a mixture as claimed in claim 2 wherein the drying step includes the shaking of the dust mixture with 8 to 12 mesh molecular-sieves and subsequently passing the sieve and dust mixture through a 60-mesh sieve to separate the molecular-sieves and large dust particles from the remainder of the dust mixture.

4. A method for determining inert content in a mixture as claimed in claim 1 and further including the step of displaying the determined rock dust percentage where the percentage is between 30 and 100%, and displaying an indication of out-of-range where the rock dust percentage is less than 30%.

5. An apparatus for determining the inert content of a coal dust and rock dust mixture comprising:
   a transparent window which is pressed against the mixture;
   a radiating means for radiating an infrared light beam through said transparent window;
   a detecting means for detecting infrared light reflected back from the dust mixture through the transparent window and for generating a signal indicating thereof;
   a normalizing means for determining a normalized value ($\phi$) of the generated signal according to the relationship $$\phi = (\log i_c - \log i_{c0})/(\log i_{c100} - \log i_{c0})$$

where
   $i_{c0}$ = measured signal at 0% rock dust
   $i_{c100}$ = measured signal at 100% rock dust
   $i_c$ = measured signal of the mixture; and
   correlating means for correlating the normalized value to a predetermined relationship of $\phi$ to rock dust percentage to determine the rock dust content of the mixture wherein said correlating means includes a means for calculating rock dust percentage (RD%) from the predetermined relationship.

$$RD\% = 100 + 30 \log_e \phi.$$

6. An apparatus for determining inert content in a mixture as claimed in claim 5 and further including a display means for displaying the RD% where the RD% in greater than 30%.

7. An apparatus for determining inert content in a mixture as claimed in claim 6 and further including a calibrating means for initially calibrating said generating means using pure samples of rock dust and coal dust for each particular utilization site.

* * * * *